United States Patent [19]

Oepen et al.

[11] Patent Number: 4,547,505

[45] Date of Patent: Oct. 15, 1985

[54] N-PHENYL-N-'-CYCLOALKYLALKANOYL-PIPERAZINE USEFUL AS ANALGETICS AND PROCESS FOR ITS PRODUCTION

[75] Inventors: Gerhard Oepen, Maintal; Jürgen Engel, Alzenau; Vladimir Jakovlev, Maintal; Klaüs Thiemer, Hanau, all of Fed. Rep. of Germany

[73] Assignee: Degussa Aktiengesellschaft, Frankfurt, Fed. Rep. of Germany

[21] Appl. No.: 583,324

[22] Filed: Feb. 24, 1984

[30] Foreign Application Priority Data

Mar. 25, 1983 [DE] Fed. Rep. of Germany ....... 3310871

[51] Int. Cl.⁴ ............... A61K 31/495; A61K 31/505; C07D 403/00; C07D 241/02
[52] U.S. Cl. ................................. 514/255; 514/256; 544/295; 544/357; 544/359; 544/360; 544/391; 546/276
[58] Field of Search ............... 544/391, 359, 360, 295, 544/357; 424/250, 251

[56] References Cited

FOREIGN PATENT DOCUMENTS

| 42366 | 12/1981 | European Pat. Off. |
| 96393 | 12/1983 | European Pat. Off. |
| 1695328 | 2/1972 | Fed. Rep. of Germany |
| 2623772 | 12/1976 | Fed. Rep. of Germany |
| 2739659 | 3/1978 | Fed. Rep. of Germany |
| 3127789 | 1/1983 | Fed. Rep. of Germany |
| 619462 | 9/1980 | Sweden |

OTHER PUBLICATIONS

Irikura, J. Med. Chem., vol. 11, 1968, pp. 801–804.
Petigara, J. Med. Chem., vol. 12, 1978, pp. 865–870.
Chem. Abst. vol. 89, 1978, item 109580c.
Irikura, Chem. Abst., 87:68418u.
Irikura, Chem. Abst., 87:68424t.
Irikura, Chem. Abst., 86:89893q.
Irikura, Chem. Abst. 87:135407e.

*Primary Examiner*—Donald G. Daus
*Assistant Examiner*—Cecilia Shen
*Attorney, Agent, or Firm*—Cushman, Darby & Cushman

[57] ABSTRACT

There are prepared new pharmacologically active compounds of the formula:

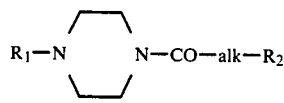

In formula I $R_1$ is a phenyl radical, pyridyl radical, a pyrimidyl group, or pyrazinyl radical, or a phenyl radical, pyridiyl radical, pyrimidyl radical, or pyrazinyl radical substituted by the radicals $R_3$ and $R_4$ which are the same or different and are hydrogen, fluorine, chlorine, bromine, trifluoromethyl, hydroxyl, $C_1$–$C_6$-alkyl groups $C_1$–$C_6$-alkoxy groups, $C_3$–$C_6$-alkenyloxy groups, $C_3$–$C_6$-cycloalkyloxy groups, phenyl-$C_1$–$C_4$-alkoxy groups, $C_1$–$C_6$-alkylmercapto groups, the nitro group, the amino group, $C_1$–$C_6$-dialkylamino groups, $C_2$–$C_6$-alkanoyl groups, $C_2$–$C_6$-alkanoylamino groups, or $C_2$–$C_6$-alkanoyloxy groups and $R_2$ is the adamantyl group, the 3,3-dimethyl-bicyclo[2.2.1]hept-2-yl radical, a saturated $C_3$–$C_{16}$-cycloalkenyl radical and alk is a straight or branched $C_1$–$C_6$ alkyl chain.

10 Claims, No Drawings

N-PHENYL-N-'-CYCLOALKYLALKANOYLPIPERAZINE USEFUL AS ANALGETICS AND PROCESS FOR ITS PRODUCTION

BACKGROUND OF THE INVENTION

There are known piperazine compounds of the formula

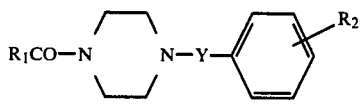

where $R_2$ is hydrogen or a chlorine atom in the 2-position and $R_1$ is a lower alkyl group, a phenyl radical, a benzyl radical or a chlorophenyl radical when Y is a single bond between the piperazine ring and the phenyl group, or where $R_1$ is a lower alkyl group, a phenyl radical a benzyl radical a chlorophenyl radical or a methoxyphenyl radical when Y is methylene, dimethylene, trimethylene, or the group —$CH_2$—CH=CH. Several of these compounds, especially those where Y is the group —$CH_2$—CH=CH— have proven to be analgetically active (J. Med. Chem. Volume 11, page 803 (1968)).

Furthermore, there are known piperazine compounds of the following formula

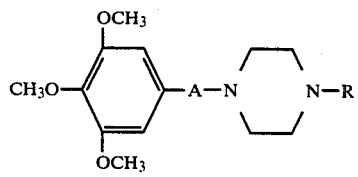

In this formula A, for example, stands for the group —$CH_2$—$CH_2$—CO— and R is a 2-chlorophenyl radical a 2-methylphenyl radical or a pyridyl-(2) radical These compounds were examined as to whether they had a suppressing action on the central nervous system (sedative and atactive actions; tranquillizing action). Several of the compounds showed activity (J. Med. Chem. Volume 12, page 867 (1969)).

Finally, there are described in German OS No. 2623772 piperazine derivatives of the general formula

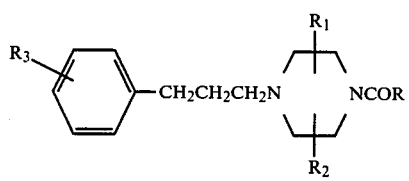

in which R is a low molecular weight straight or branched chain alkyl group having 1 to 6 carbon atoms, a low molecular weight, straight or branched chain alkenyl group having 2 to 5 carbon atoms, a cycloalkyl group having 3 to 6 carbon atoms, a low molecular weight, straight or branched chain alkyl group having 1 to 6 carbon atoms which is joined to a low molecular weight, straight or branched chain alkoxy group having 1 to 6 carbon atoms or a hydroxy group, a low molecular weight, straight or branched chain alkenyl group having 2 to 5 carbon atoms which is joined to a low molecular weight, straight or branched chain alkoxy group having 1 to 6 carbon atoms, or a tetrahydrofuryl group; $R_1$ and $R_2$, which can be the same or different are hydrogen or low molecular weight, straight or branched chain alkyl groups having 1 to 4 carbon atoms (with the proviso that both groups $R_1$ and $R_2$ cannot be a hydrogen atom); and $R_3$ is a hydrogen atom, a halogen atom, a low molecular weight, straight or branched chain alkyl group having 1 to 4 carbon atoms, a low moleclar weight, straight or branched chain alkoxy group having 1 to 4 carbon atoms or a hydroxy group.

These compounds are stated to have an analgetic action, in which case however, it is a matter of peripherally active materials. In contrast the compounds of the invention are centrally active analgetics.

SUMMARY OF THE INVENTION

The invention is directed to compounds of the formula

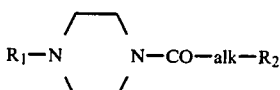

where $R_1$ a phenyl group, pyridyl group, pyrimidyl group or pyrazinyl group or a phenyl group, pyridyl group, pyrimidyl group, or pyrazinyl group substituted by the radicals $R_3$ and $R_4$ which are the same or different and are hydrogen, fluorine, chlorine, bromine, trifluoromethyl, hydroxyl, $C_1$–$C_6$ alkyl group, $C_1$–$C_6$-alkoxy groups, $C_3$–$C_6$-alkenyloxy group, $C_3$–$C_6$-cycloalkyloxy groups, phenyl-$C_1$–$C_4$-alkoxy groups, $C_1$–$C_6$-alkylmercapto groups, the nitro group, the amino group, $C_1$–$C_6$-alkylamino groups, $C_1$–$C_6$-dialkylamino groups, $C_2$–$C_6$-alkanoyl groups, $C_2$–$C_6$-alkanoylamine groups or $C_2$–$C_6$-alkanoyloxy groups and $R_2$ is the adamantyl group, the 3,3-dimethylbicyclo[2,2.1]hept-2-yl group, a saturated $C_3$–$C_{16}$-cycloalkyl group or a single unsaturated $C_3$–$C_{16}$-cycloalkenyl group and alk is a straight or branched $C_1$–$C_6$-alkylene chain and their physiologically (or pharmaceutically) acceptable salts.

The invention also includes the preparation of compounds of formula I(a) by reacting a compound of the formula

where Z is the group $R_1$ or —CO—alk—$R_2$ with a compound of the formula $$Z'X \qquad \text{III}$$

where X is a halogen atom, e.g. chlorine, bromine, or iodine, when Z' is the group $R_1$ and Z the group —CO—alk—$R_2$ or where X is a halogen atom or is the group —OR, when Z' is the group —CO—alk—$R_2$ and Z is the group $R_1$ and R is hydrogen, a $C_1$–$C_6$-alkyl group, a benzyl group or a phenyl group or a phenyl group substituted by chlorine, bromine, the nitro group, or $C_1$–$C_4$ alkyl group, or (b) by reacting a compound of the formula $$R_2\text{—alk—CO—N(CH}_2\text{—CH}_2\text{Hal})_2 \qquad \text{IV}$$

where Hal is a halogen atom with a compound of the formula $$R_1NH_2 \qquad V$$

and optionally reducing a nitro group in the compound obtained to the amino group and/or optionally acylating, and/or alkylating or alkenylating the compound obtained and/or converting it into the acid addition salt.

The invention furthermore is directed to medicines containing compounds of formula I together with conventional carriers and/or diluents or adjuvants.

Also the invention includes a process for the production of a medicine comprising processing a compound of formula I with customary pharmaceutical carriers or diluents to form pharmaceutical perparations.

Additionally, the invention includes the use of the compounds of formula I for the production of medicines.

The compounds of the invention are active pharmacologically or pharmacotherapeutically. For example, they are analgetically active. They possess a wide therapeutic breadth and furthermore are characterized by the lack of central nervous system side effects such as for example, sedation and ataxia. The compound of the invention are centrally active analgetics. Tolerance experiments show that the compounds of the invention are not habit forming. The analgetic action is not like opiates, that is the compounds of the invention do not show affinity for the opiate receptor (for example no antagonism of the analegesic when there is subsequently dispensed Naloxon). Furthermore, the compounds of the invention arrest the secretion of gastric juice and are antiulcerative and antiphlogistically active.

Thus the invention is directed to making available compounds having favorable pharmacological properties which are useful as medicines.

The alkyl radicals occuring in the compounds of formula I (for example as the alkyl group or in the form of the alkoxy group, the alkylmercapto group, the alkylamino group, the dialkyamino group of the phenalkoxy group) and alkenyloxy radical as well as the alkylene chain can be straight or branched. In the event that the radicals $R_3$ and/or $R_4$ are alkyl groups or contain alkyl radicals, these consist of especially 1 to 4 carbon atoms (methyl, ethyl, propyl, isopropyl, or butyl groups). Illustrative of specific groups are methyl, ethyl, propyl, isopropyl, butyl, sec.butyl, amyl, or hexyl, methoxy, ethoxy, propoxy, isopropoxy, butoxy, amyloxy, hexoxy, methylamino, ethylamino, propylamino, butylamino, sec.butylamino, hexylamino, dimethylamono, diethylamino, methyl ethyl amono, diisopropylamino, dipropylamino, dibutylamino, diamylamino, dihexylamino, methylmercapto, ethylmercapto, propylmercapto, butylmercapto, hexylmercapto, allyloxy, methallyloxy, crotyloxy, benzyloxy, phenethoxy, phenpropoxy, phenbutoxy.

The chain alk indicates an alkylene group such as for example, the methylene, dimethylene, trimethylene, tetramethylene, pentamethylene, or hexamethylene group or also for example, the group

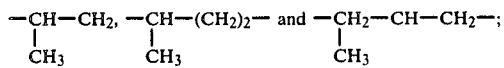

particularly the chain alk consists of 1,2 or 3 C-atoms. In case the radical $R_3$ or $R_4$ is a $C_3$-$C_6$-alkenyloxy group, the alkenyl portion especially consists of 3 or 4 carbon atoms. In the event that the radical $R_2$ represents a $C_3$-$C_{16}$ cycloalkyl radical, it is for example, cyclopropyl, cyclobutyl,, cyclopentyl, cyclohexyl, cycloheptyl cyclooctyl, cyclononyl, or cyclodecyl, or cyclododecyl or cyclohexadecyl. In case the radicals $R_3$ and $R_4$ are $C_3$-$C_6$-cycloalkoxy groups, they are cyclopropoxy, cyclobutoxy, cyclopentoxy, or cyclohexoxy groups.

In the event the radicals $R_3$ and $R_4$ are alkanoyloxy groups, alkanoylamino groups or alkanoyl group, the alkanoyl radical especially consists of 2 to 4 carbon atoms (for example, the acetyl radical, propionyl radical, butyryl radical, valeroyl or hexanoyl). Illustrative groups are acetoxy, propionoxy, butyroxy, valeroxy, hexanoyloxy, acetamibno, propionamino, butyramino, valeramino, or hexanoylamino.

The pyridyl group ($R_1$) is preferably joined via the 2-position with the piperazine group. The same is true in regard to the pyrimidyl and pyrazinyl groups. The radicals $R_3$ and $R_4$ can be on the 2, 3 and/or 4 position of the phenyl group $R_1$. In the event this phenyl group contains a substituent, this is preferably in the 2-position, in the case where there are two substituents $R_3$ and $R_4$, are preferably in the 2,6-positions of the phenyl group. Especially favorably activities are shown by compounds of formula I where one or both substituents $R_3$ and/or $R_4$ are $C_1$-$C_6$-alkoxy groups, especially $C_1$-$C_4$ alkoxy group, $C_2$-$C_6$-alkanoylamino groups, especially $C_2$-$C_4$-alkanoylamino groups, or fluorine or chlorine, alk contains 2 or 3 C-atoms and $R_2$ is a cyclohexyl radical. At the same time $R_3$ and $R_4$ contain the same or different substituents of the types mentioned. In case $R_1$ is pyridyl group or a pyrazinyl group and these groups contain a substituent $R_3$, it is located preferably in the 6-position of the pyridyl or pyrazinyl group. With 2 substituents the pyridyl group is preferably substituted in the 3 and 6 position and the pyrazinyl group is preferably substituted in the 5 and 6 positions by the substituents $R_3$ and $R_4$.

The products of the process can optionally be alkylated or alkenylated. Hereby, for example, there is introduced a $C_1$-$C_6$-alkyl group, a $C_3$-$C_6$ cycloalkyl group, a phenyl-$C_1$-$C_4$-alkyl group or a $C_3$-$C_6$-alkenyl group in compounds where $R_3$ and/or $R_4$ is an amino or monoalkylamino group or a hydroxy group.

This alkylation is carried out in known manner. As alkylating agents there can be employed for example, esters of the formula R'Hal, ArSO$_2$OR' and SO$_2$(OR')$_2$, whereby Hal is a halogen atom (especially chlorine, bromine, or iodine) and Ar is an aromatic radical such as for example, a phenyl or naphthyl residue which optionally is substituted by one or more lower alkyl groups (e.g., methyl, ethyl, propyl, butyl, or hexyl) and R' is a $C_1$-$C_6$-alkyl group, a $C_3$-$C_6$-alkenyl group, a $C_3$-$C_6$-cycloalkyl group or a phenyl $C_1$-$C_4$-alkyl group. Examples are p-toluenesulfonic acid-$C_1$-$C_6$-alkyl esters (e.g., methyl p-toluene sulfonate, hexyl p-toluene sulfonate, p-toluenesulfonic acid-$C_3$-$C_6$-alkenyl esters (e.g., alkyl p-toluenesulfonate, methallyl p-toluenesulfoate), $C_1$-$C_6$-dialkyl sulfates (e.g., dimethyl sulfate, diethyl sulfate), $C_1$-$C_6$-alkyl halides (e.g., methyl chloride, methyl bromide, methyl iodine, ethyl bromide, ethyl chloride, ethyl iodide), $C_3$-$C_6$-alkenyl halides, e.g. allyl chloride, $C_3$-$C_6$-cycloalkyl halides (e.g., cyclopropyl chloride, cyclopropyl bromide, cyclohexyl chloride), cyclohexyl chloride), phenyl-$C_1$-$C_4$-alkyl halides (e.g., benzyl chloride, benzyl bromide) and the like. The alkylation reaction is optionally carried out with the addition of customary acid binding agents such as alkali carbonates ($K_2CO_3$), alkali hydroxides (NaOH, KOH), pyridine or other customary tertiary amines at temperatures between 0° and 200° C., preferably 20° to 150° C., in an inert solvent such as lower alcohols (methanol, ethanol, isopropanol), lower ketones (acetone methyl ethyl ketone), lower haloalkanes (chloroform, methylene chloride, dichloroethane), dioxane, dimethyl formamide, dimethyl sulfoxide, aromatic hydrocarbons (benzene, toluene, xylene) or pyridine.

This alkylation can also be carried out by first producing an alkali compound of the compound of formula I to be alkylated wherein for example, $R_3$ and/or $R_4$ is an amino, monoalkylamino, or hydroxy group, by reacting it in an inert solvent such as dioxane, tetrahydrofurane, dimethyl formamide, benzene, toluene, or xylene or in liquid ammonia with alkali metal, alkali hydride, or alkali amide (especially sodium or sodium compounds) at temperatures between −70° and 120° C. and then adding the alkylating agent (for example $C_1$–$C_6$-alkyl iodide or $C_1$–$C_6$-alkyl bromide) at a temperature between −70° and +50° C.

The alkylation can also be carried out in the presence of tetraalkyl ammonium salts (especially the halides) in combination with alkali hydroxides at temperatures between 0°–100° C., preferably 20°–80° C. in an aprotic solvent or also in chloroform or methylene chloride. As aprotic solvent there can be used for example: tertiary amides (dimethyl formamide, N-methyl pyrrolidone, hexamethyl phosphoric acid triamide), dimethyl sulfoxide, acetonitrile, dimethoxyethane, acetone, or tetrahydrofurane.

In those products of formula I wherein $R_3$ and/or $R_4$ is an amino group or a hydroxy group by acylation, there can be introduced a $C_2$–$C_6$-alkanoyl group into the amino or hydroxy group. This acylation for example is carried out in known manner for this type of process using $C_2$–$C_6$-alkanoyl halides or $C_2$–$C_6$alkanoyl anhydrides. For example, this acylation is carried out in a solvent or suspension agent (aliphatic halohydrocarbons such as chloroform or dichloromethane, lower aliphatic ketones, dioxane, dimethyl formamide, benzene, toluene) in the presence of an acid binding material (pyridine, trialkylamine, alkali carbonate, alkali bicarbonate, alkaline earth carbonate, alkali acetate) at temperatures between 0°–180° C., preferably 0°–100° C. Optionally the acylation can be carried out in such manner that there is first produced an alkali compound of the compound to be acylated by reacting it in an inert solvent such as dioxane, dimethyl formamide, benzene, or toluene with an alkali metal, alkali hydride, or alkali amide (especially sodium or sodium compounds) at temperatures between 0° and 150° C. and then the acylating agent (for example the alkanoyl halide) is added.

In place of the acylating agents mentioned there can also be used other chemically equivalent agents used in chemistry (see for example, also L. F. and Mary Fieser "Reagents for Organic Synthesis", John Wiley and Sons, Inc., New York 1967, Volume 1, pages 1303–1304 and Volume 2, page 471). It is understood that acyl groups in the compounds obtained can also be split off again, for example, with aqueous alkali or alcoholic alkali liquor (for example, methanolic KOH) or also optionally by means of mineral acids such as hydrochlorine acid or sulfonic acid in alcoholic or aqueous-alcoholic solution at temperatures between 20° and 100° C.

In the case of those products where the radicals $R_3$ and/or $R_4$ signify nitro grouops, these can be reduced to the corresponding amino groups.

Catalytic hydrogenation is especially considered for this reduction. As catalysts there can be used: Raney nickel, noble metals such as palladium and platinum, as well as compounds thereof with or without carriers such as for example barium sulfate, calcium sulfate, etc. It is recommended to carry out the hydrogenation of the nitro group at temperatures between 20° and 80° C. and a pressure of approximately 5–50 atmospheres absolute in a solvent for example, alcohols, dioxane, tetrahydrofurane, etc. It can be advantageous in many cases for the subsequent isolation of the reduced compounds if there are added to the mixture being hydrogenated, drying agents such as sodium or magnesium sulfate. However, the reduction can also be carried out with nascent hydrogen, for example, zinc/hydrochloric acid, tin/hydrochloric acid, iron/hydrochloric acid or with salts of hydrogen sulfide in alcohol/water at about 70 to about 120° C. or with activated aluminum in aqueous ether at 20° to 40° C. or with tin (II) chloride hydrochloric acid.

In regard to process (a):

This process is generally carried out in an inert solvent or suspension agent at temperatures between 0°–250° C., especially 5°–180° C., preferably 20°–150° C. As solvents there can be employed for example: saturated alicyclic and cyclic ethers (dioxane, tetrahydrofurane, lower dialkyl ethers such as diethyl ether, diisopropyl ether), lower alkanols such as ethanol, isopropanol, butanol, lower aliphatic ketones (acetone, methyl ethyl ketone), lower aliphatic hydrocarbons or halohydrocarbons (methylene chloride, chloroform, 1,2-dichloroethane) aromatic hydrocarbons (benzene, toluene, xylene), lower dialkyl amides of lower saturated aliphatic carboxylic acids (dimethyl formamide, dimethyl acetamide), tetramethyl urea, N-methyl pyrrolidone, dimethyl sulfoxide, or mixtures of these agents.

In case X is a halogen atom it is especially a matter of chlorine, bromine, or iodine, preferably chlorine or bromine.

Generally the reactants are reacted in molar amounts. However, optionally it can be suitable to employ one reactant in slight excess. This is especially true in case the compound of formula III represents a carboxylic acid ester $R_2$—alk—CO—OR, whereby R is a lower alkyl group. (In this case it is recommended, optionally to continuously remove the lower alcohol formed in the reaction.) Optionally the reaction can also be carried out in the presence of basic or acid binding agents such as alkali carbonates (potash, soda) alkali hydrogen carbonates, alkali acetates, alkali hydroxides, or tertiary amines (for example, triethylamine). The latter is especially true if compounds of formula III are employed wherein X is a halogen atom.

In a given case, it is also favorable to add condensation agents such as dicyclohexyl carbodiimide, tetraethyl pyraphosphite, 5-(3'-sulfonephenyl)-ethyl-isooxazole, sulfurous acid-bisalkyl amides (for example $SO[N(CH_3)_2]_2$) or N,N'carbonyl-diimidazole (in case for example X is OH). In case R represents a substituted phenyl radical, this preferably contains one or two of the stated substituents, whereby these preferably are located in the 3 and/or 4-position of the phenyl radical. Unknown starting materials of formula III wherein X is a halogen atom (preferably chlorine or bromine) and Z' is the group —CO—alk—R₂, can be obtained in known manner for example, from the corresponding acids by reaction with thionyl chloride or thionyl bromide. For example, there is given the production of 3-cyclohexyl propionyl chloride:

Within 45 minutes there is dropped into 135.6 grams (1.14 moles) of thionyl chloride 60 grams (0.38 mole) of 3-cyclohexyl propionic acid. After the ending of the dropping in, the mixture was stirred for a further 2 hours at 50° C. Subsequently the excess thionyl chloride was concentrated in a vacuum and the residue remaining reacted without purification.

Those starting materials of formula III wherein X is the group OR and Z' the group —CO—alk—R₂ can be produced in the customary manner from the just mentioned acid chlorides or acid halides by reaction with compounds HOR or their metal salts (alkali salts) (see in regard to this Organikum, Organisch Chemisches Grundpraktikum, VEB; Deutscher Verlag der Wissenschaften Berlin, 9th edition 1976, pages 400 et seq.). Unknown starting materials of formula II wherein Z is the group —CO—alk—R₂ can be produced for example, by reaction of benzyl pyperazine with the corresponding acid chlorides R₂—alk—COCl and subsequent debenzylation. The reaction of the benzyl piperazine with the acid chloride for example is carried out at 0° C. in acetone as solvent. After removing the solvent the thus obtained crude product is taken up in methanol, treated with Pd/C and debenzylated at 5 bar and 40° C. After filtering off the catalyst the solvent is distilled off in a vacuum. The product produced in this manner can be further processed without additional working up.

In regard to Process (b):

This process is preferably carried out in a polar solvent at temperatures between 40°-200° C. Preferably it is performed in the presence of an acceptor for the hydrohalide formed in the course of the reaction. As acid acceptors there can be used for example: alkali carbonates ($K_2CO_3$, $Na_2CO_3$, $NaHCO_3$), tertiary amines such as triethylamine, pyridine, alkali acetate, alkali hydroxide. Hal in the starting compound for this process preferably means chlorine or bromine.

As solvents there can be used for example: lower alkanols (ethanol, isopropanol, butanol, isoamyl alcohol), lower alicyclic or cyclic ethers (diethyl ether, dioxane, tetrahydrofurane), diethylene glycol, di-$C_1$-$C_4$-alkyl ethers (dimethyl ether of diethylene glycol), lower dialkyl amides of lower saturated aliphatic carboxylic acids (dimethyl formamide, dimethyl acetamide), tetramethyl urea, N-methyl pyrrolidone, dimethyl sulfoxide as well as mixtures of these agents.

Starting materials of formula IV can be obtained for example, from acid chlorides of the formula R₂—alk—COCl and an amine of the formula HN(CH₂—CH₂—Hal)₂, in the customary manner. Hal is preferably chlorine, bromine, or iodine. For this purpose for example, there are reacted equimolar amounts of the corresponding acid chloride, N-(bis-2-haloethyl)-amine acid and triethylamine at 0° C. in acetone as a solvent. Then the mixture is stirred for a further 8 hours at room temperature. Then the triethylamine hydrochloride formed is filtered off and the filtrate concentrated in a vacuum. The residue formed, without further purification is reacted with the corresponding anilines to the compounds of the invention as described in Example 39. For example, the N-(bis)-2-chloroethyl)-3-cyclohexyl-propionamide is produced as follows: 10 ml of acetone were slowly dropped into a mixture of 0.01 mole (1.8 gram) of N-(bis-chloroethyl)-amine-hydrochloride, 0.02 mole (1 gram) of triethylamine and 0.01 mole (1.7 gram) of 3-cyclohexyl-propionyl chloride in 50 ml of acetone cooled to 0° C. After the end of the dropping in, stirring was continued for a further 8 hours at room temperature. Then the triethylamine hydrochloride formed was filtered off and the filtrate concentratd in a vacuum. The product thus obtained, without further purification, was reacted with 0.03 mole (1.2 grams) of 3-methoxyaniline, as described in Example 39.

Depending on the process conditions and the starting material, there are obtained the final product of formula I either in the free form or in the form of their salts. The salts of the final products can be again converted into the bases in known manner, for example with alkali or ion exchangers. From the bases there can be obtained salts by reaction with organic or inorganic acids, especially those which are suitable for formation of therapeutically useful salts. As such acids, there can be mentioned: hydrohalic acids, e.g. hydrochloric acid, hydrobromic acid, acids of sulfur, sulfuric acid, sulfurous acid, acids of phosphorus, phosphoric acid, phosphorous acid, nitric acid, perchloric acid, organic mono-, di-, or tricarboxylic acids of the aliphatic, alicyclic, aromatic, or heterocyclic series as well as sulfonic acids. Examples of these are: formic acid, acetic acid, propionic acid, succinic acid, glycolic acid, lactic acid, malic acid, tartaric acid, citric acid, ascorbic acid, maleic acid, fumaric acid, hydroxymaleic acid, pyruvic acid, phenyl acetic acid, benzoic acid, p-aminobenzoic acid, anthranilic acid, p-hydroxybenzoic acid, salicylic acid, or p-aminosalicylic acid, embonic acid, methanesulfonic acid, ethanesulfonic acid, hydroxyethanesulfonic acid, ethylenesulfonic acid, halobenzenesulfonic acid, e.g. p-chlorobenzenesulfonic acid, toluenesulfonic acid, naphthalenesulfonic acid, or sulfanilic acid or even 8-chlorotheophylline.

Those compounds which contain asymmetric carbon atoms and are usually produced as racemates may be split into the optically active isomers in a known manner, for example, by means of an optically active acid. However, it is also possible to use an optically active or also diastereomeric starting material from the beginning, in which case a corresponding pure optically active or diastereomeric configuration is obtained as the end product.

Diastereomeric racemates can also occur, in case there are present two or more asymmetrical carbon atoms in the compounds produced. Separation is possible in customary manner, for example by recrystallization.

The compounds according to this invention are suitable for the preparation of the pharmaceutical compositions or preparations. The pharmaceutical compositions or medicaments contain an active principle one or more of the compounds according to the invention, optionally in admixture with other pharmacologically or pharmaceutically active substances. The medicaments are prepared in known manner with the usual pharmaceutical additives and other conventional excipients and diluents.

Examples of excipients and additives of this kind are the substances recommended and specified in the following literature references as additives for pharmacy, cosmetics and related fields: Ullmanns Encyklopadie der technischen Chemie, Volume 4 (1953), pages 1–39; Journal of Pharmaceutical Sciences, Volume 52 (1963), pages 918 et seq.; H. V. Czetsch-Lindenwald, Hilfsstoffe fur Pharmazie und angrenzende Gebiete; Pharm. Ind., No. 2, 1961, pages 72 et. seq.; Dr. H. P. Fiedler, Lexikon der Hilfsstoffe fur Pharmazie, Kosmetic und angrenzende Gebiete Cantor KG. Aulendorf (Wurtt.)

Examples of such materials include gelatin, natural sugars such as sucrose or lactose, lecithin, pectin, starch (for example cornstarch), alginic acid, tylose, talc, lycopodium, silica (for example collodial silica), glucose, cellulose, cellulose derivatives, for example cellulose ethers in which the cellulose hydroxyl groups ar partially etherified with lower aliphatic alcohols and/or lower saturated oxyalcohols (for example, methyl hydroxypropyl cellulose, methyl cellulose, hydroxyethyl cellyulose), stearates, e.g. methyl stearate and glyceryl stearate, magnesium and calcium salts of fatty acids with 12 to 22 carbon atoms, especially saturated acids (for example, calcium stearate, calcium laurate, magnesium oleate, calcium palmitate, calcium behenate, and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono, di, and triglycerides of saturated fatty acids ($C_{12}H_{24}O_2$ to $C_{18}H_{36}O_2$ and their mixtures), e.g., glyceryl monostearate, glyceryl distearate, glyceryl tristearate, glyceryl trilaurate, pharmaceutically compatible mono- or polyhydric alcohols such as glycerine, mannitol, sorbitol, pentaerythritol, ethyl alcohol, diethylene glycol, triethylene glycol, ethylene glycol, propylene glycol, dipropylene glycol, polyethylene glycol 400, and other polyethylene glycols as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atom alkanols), mannitol, ethyl alcohol, butyl alcohol, octadecycl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case, also be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially medium viscosity dimethyl polysiloxane), magnesium carbonate and the like.

As further adjuvants there can be used materials which cause decomposition (so-called explosive agents) such as: cross-linked polyvinyl pyrrolidine, sodium carboxymethyl starch, or microcrystalline cellulose. Likewise there can be used encasing agents such as for example: polyacrylic ester, cellulose ether and the like.

For the production of solutions, there can be used water or physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g., glyceryl oleate, glyceryl stearate, glyceryl palmitate, and glyceryl acetate, partial esters of glycerine, e.g., glyceryl monostearate, glyceryl distearate, glyceryl monopalmitate, paraffins, and the like.

In the production of the composition, there can be used known and customary solution aids or emulsifiers. As solution aids and emulsifiers, there can be used, for example, polyvinyl pyrrolidone, sorbitan fatty acid esters such as sorbitan trioleate, lecithin, gum acacia, gum tragacanth, polyoxyethylated sorbitan monooleate, polyoxyethylated fats, polyoxyethylated oleotriglycerides, linolized oleotriglycerides, polyethylene oxide-condensation products of fatty alcohols, alkylphenols or fatty acids or also 1-methyl-3-(2-hydroxyethyl)-imidazolidone-2. As used herein, polyoxyethylated means that the materials in question contain polyoxyethylene chains whose degree of polymerization generally is between 2 and 40, particularly between 10 and 20.

Such polyoxyethylated materials, for example, can be obtained by reaction of hydroxyl group containing compounds (for example, mono- or diglycerides) or unsaturated compounds such as, for example, those containing the oleic acid radical with ethylene oxide (for example, 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191-195.

Furthermore, there can be added preservatives, stabilizers, buffers, for example, calcium hydrogen phosphate, collodial aluminum hydroxide, taste correctives, antioxidants and complex formers (for example, ethylene diamine tetraacetic acid) and the like. In a given case for stabilization of the active molecule, the pH is adjusted to about 3 to 7 with physiologically compatible acids or buffers. Generally, there is preferred a neutral to weak acid (to pH 5) pH value.

As antioxidants, there can be used, for example, sodium meta bisulfite, ascorbic acid, gallic acid, alkyl gallates, e.g., methyl gallate and ethyl gallate, butyl hydroxyanisole, nordihydroguaiaretic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives, there can be used, for example, sorbic acid, p-hydroxybenzoic acid esters (for example, lower alkyl esters such as the methyl ester and the ethyl ester), benzoic acid, sodium benzoate, trichloroisobutyl alcohol, phenol, cresol, benzethonium chloride, and formalin derivatives.

The pharmacological and galenical treatment of the compounds of the invention is carried out according to the usual standard methods. For example, the active material or materials and assistants or carriers are well mixed by stirring or homogenization (for example, by means of customary mixing apparatus, e.g., a colloid mill or ball mill), wherein the operation is generally carried out at temperatures between 20° and 80° C., preferably 20° to 50° C., especially at room temperature. Besides, reference is made to the following standard textbook: Sucker, Fuchs, Speiser, Pharmazeutische Technologie, Thieme-Verlag, Stuttgart, 1978.

The active principles of medicaments may be applied to the skin or mucosa or into the interior of the body, for example orally, enterally, pulmonarily, rectally, nasally, vaginally, lingually, intravenously, intra-arterially, intracardially, intramuscularly, intraperitoneally, intracutaneously, or subcutaneously.

The compounds of the invention show a good analgetic action in the electro pain test, mouse (B. Blake et al, Med, exp., Volume 9, page 146, (1963) or Haffner test, mouse (F. Haffner, Dtsch. Med. Wschr., Volume 55, page 731 (1929).

For example, in the above-mentioned test procedures there is obtained the analgetic action at a dosage of 20 mg/body weight kg mouse per os.

This analgetic action is comparable with the action of the known medicines Pethidin and Pentazocine.

The lowest clearly effective dosage (activity as stated above) in the above-mentioned animal experiments is for example:

5 mg/kg orally
0.5 mg/kg intravenously

As a general dosage range for the above-mentioned activities (animal experiments as above) there can be used:

5–100 mg/kg orally, especially 10–40 mg/kg
0.5–10 mg/kg intravenously, especially 0.1–4 mg/kg.

The compounds of the invention are indicated for pains due to various causes such as postoperative pains, wounds, and toothaches.

The pharmaceutical preparation generally contain between 0.5 and 150 mg, preferably 10 to 100 mg of the active components of the invention.

The preparations may be administered, for example, in the form of tablets, capsules, pills, dragees, suppositories, ointments, jellies, creams, powders, dusting powders, aerosols, or in liquid form. Examples of liquid formulations are oily or alcoholic or aqueous solutions, suspensions and emulsions. Preferred formulations are tablets containing from 10 to 50 mg or active substance, or solutions containing from 1 to 10% of active substance.

The active components according to the present invention may be used in individual doeses of, for example:

(a) from 5 to 100 mg, preferably from 10 to 50 mg in the case of oral formulations,
(b) from 0.5 to 10 mg, preferably from 1 to 5 mg in the case of parenteral formulations (for example intravenously, intramuscularly),
(c) from 0.5 to 300 mg, preferably from 10 to 100 mg in the case of formulations for rectal or vaginal application. (the doses are based on the free base in each case).

For example, 1 to 3 tablets containing from 10 to 50 mg of active substance may be prescribed three times daily or, for example, in the case of intravenous injection, a 1 to 10 ampoule containing from 1 to 5 mg of active substance may be prescribed one to five times daily. In the case of oral administration, the minimum daily dose is, for example, 30 mg, while the maximum daily dose should not exceed 1 gram.

For the treatment of dogs and cats the individual dosage orally is generally between about 1 and 100 mg/kg body weight. The parental dosage is between about 0.1 and 10 mg/kg body weight.

For the treatment of horses and cattle the individual dosage orally is generally between about 1 and 100 mg/kg; the parenteral individual dosage is between about 0.1 and 10 mg/kg body weight.

The acute toxicity of the compounds of the invention on the mouse (expressed by the LD 50 mg/kg; method according to Miller and Tainter: Proc. Soc. Exper. Biol. a. Med., Volume 57 (1944), page 261 for example, with oral application is between 100 and 2500 mg/kg (or above 2500 mg/kg).

The medicaments may be used in human medicine, veterinary medicine, or in agriculture, either individually or in admixture with other pharmacologically active substances.

Unless otherwise indicated, all parts and percentages are by weight.

The compositions can comprise, consist essentially of, or consist of the stated materials set forth.

The methods can comprise, consist essentially of, or consist of the steps set forth with the materials shown.

DETAILED DESCRIPTION

Example 1 (Process a)

1-(3-methoxy-phenyl)-4-(3-cyclohexyl-propionyl)-piperazine

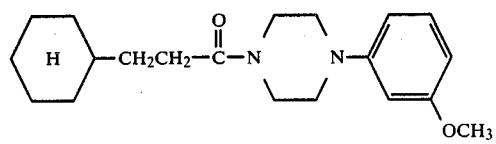

There was dropped into a mixture of 0.06 mole (11.5 grams) of N-(3-methoxyphenyl)-piperazine and 0.06 mole (6.1 grams) of triethylamine in 100 ml of absolute toluene with stirring at room temperature 0.06 mole (10.5 grams) of 3-cyclohexylpropionyl chloride. After the end of the dropping in, stirring was continued at room temperature for a further 3 hours. The triethylammonium hydrochloride formed was filtered off and the filtrate concentrated in a vacuum. The residue was dissolved in 60 ml of acetone and treated dropwise with 11 ml of 6N isopropanolic hydrochloric acid. The hydrochloride precipitated out and was recrystallized from methyl ethyl ketone.

Yield: 9.9 grams.

M.P. of the hydrochloride: 175°–176° C.

In another embodiment the procedure can be as follows:

II

A mixture of 0.05 mole (7.8 grams) of 3-cyclohexyl-propionic acid, 0.05 mole (9.6 grams) of N-(3-methoxyphenyl)-piperazine and 0.05 mole (10.3 grams) of N,N-dicyclohexyl-carbodiimide dissolved in 150 ml of water-free methylene chloride was stirred for 7 days at room temperature. After the end of the reaction the dicyclohexylurea formed was filtered off, the filtrate concentrated in a vacuum and the crude product converted into the hydrochloride as described above.

Yield: 3.7 grams.

M.P. of the hydrochloride: 175°–176° C.

III

A mixture of 0.05 mole (8.5 grams) of 3-cyclohexyl-propionic acid methyl ester and 0.06 mole (11.5 grams) of N-(3-methoxyphenyl)-piperazine dissolved in 100 ml of toluene was heated under reflux for 8 hours, whereby the alcohol ($CH_3OH$) formed in the reaction was distilled off. After the end of the reaction the solvent was drawn off in a vacuum. The crude product was converted into the hydrochloride in the manner described through addition of 6N isopropanolic HCl and the hydrochloride was recrystallized from methyl ketone for further purification.

Yield: 4.6 grams.

M.P. of the hydrochloride: 175°–176° C.

In the manner analogous to Example 1 (according to Process a) the following compounds of formula I set forth in Table 1 were obtained:

| Example | Product R₁ | R₂ | alk | Yield in g | M.P. (0° C.) | Starting Materials |
|---|---|---|---|---|---|---|
| 2 | 2-OCH₃-phenyl | Cyclohexyl | (CH₂)₂ | 12,3 | 144–145 (HCl-Salt) | 11.5 g N—(o-Methoxy-phenyl)-piperazine 10,5 g 3-cyclohexyl-propionyl chloride |
| 3 | 2-OCH₃-phenyl | Cyclohexyl | CH₂ | 10,9 | 150–153 (HCl-Salt) | 7,8 g 2-Cyclohexyl-acetic acid and 9,6 g N—(2-Methoxy-phenyl)-piperazine |
| 4 | 2-OCH₃-phenyl | 3,3-Dimethyl-bicyclo[2.2.1]hept-2-yl | (CH₂)₂ | 9,0 | 198–199 (HCl-Salt) | 11,5 g (2-Methoxy-phenyl)-piperazine and 12,9 g 3-(3,3-Dimethyl-bicyclo-[2.2.1]-hept-2-yl)-propionyl chloride |
| 5 | 2-OC₂H₅-phenyl | As in Example 4 | (CH₂)₂ | 5,3 | 175 (HCl-Salt) | 12,4 g N—(2-Ethoxy-phenyl)-piperazine and 12,9 g 3-(3,3-Dimethyl-bicyclo-[2.2.1]-hept-2-yl)-propionyl chloride |
| 6 | 2-OCH₃-phenyl | As in Example 4 | CH₂ | 11,8 | 183–187 (HCl-Salt) | 11,5 g N—(2-Methoxy-phenyl)-piperazine and 11 g (3,3-Dimethyl-bicyclo-[2.2.1]-hept-2-yl)-acetyl chloride |
| 7 | 2-OC₂H₅-phenyl | As in Example 4 | CH₂ | 10,1 | 107 (Base) | 12,4 g N—(2-Ethoxy-phenyl)-piperazine and 11 g (3,3-Dimethyl)-bicyclo-[2.2.1]-hept-2-yl)-acetyl chloride |
| 8 | 2-OCH₃-phenyl | Cyclopentyl | (CH₂)₂ | 4,9 | 155–156 (HCl-Salt) | 9,6 g N—(2-Methoxy-phenyl)-piperazine and 7,1 g 3-Cyclopentyl-propionic acid |
| 9 | 2-OC₂H₅-phenyl | Cyclopentyl | (CH₂)₂ | 4,8 | 134–136 (HCl-Salt) | 10,3 g N—(2-Ethoxy-phenyl)-piperazine and 7,1 g 3-Cyclopentyl-propionic acid |
| 10 | 2-OC₂H₅-phenyl | Cyclohexyl | (CH₂)₂ | 12,6 | 147–148 (HCl-Salt) | 12,4 g N—(2-Ethoxy-phenyl)-piperazine and 10,5 g 3-Cyclohexyl-propionyl chloride |
| 11 | 2-OC₃H₇-phenyl | Cyclohexyl | (CH₂)₂ | 9,2 | 146 (HCl-Salt) | 13,2 g N—(2-n-Propyloxy-phenyl)-piperazine and 10,5 g 3-Cyclohexyl-propionyl chloride |
| 12 | 2-OCH(CH₃)₂-phenyl | Cyclohexyl | (CH₂)₂ | 5,2 | 59–63 (Base) | 13,2 g N—(2-Isopropyloxyphenyl)-piperazine and 10,5 g 3-cyclohexyl-propionyl chloride |

-continued

| Example | R₁ | Product R₂ | alk | Yield in g | M.P. (0° C.) | Starting Materials |
|---|---|---|---|---|---|---|
| 13 | 2-(OCH₂—CH=CH₂)-phenyl | Cyclohexyl | (CH₂)₂ | 8,3 | 37–39 (Base) | 13 g N—(2-Allyloxy-phenyl)-piperazine and 10,5 g 3-Cyclohexyl-propionyl chloride |
| 14 | 2-(cyclohexyloxy)-phenyl | Cyclohexyl | (CH₂)₂ | 5,0 | 70–72 (Base) | 15,6 g N—(2-Cyclohexyloxy-phenyl)-piperazine and 10,5 g 3-Cyclohexyl-propionyl chloride |
| 15 | 2-(OCH₂C₆H₅)-phenyl | Cyclohexyl | (CH₂)₂ | 11,5 | 86–87 (Base) | 16,8 g N—(2-Benzyloxy-phenyl)-piperazine and 10,5 g 3-Cyclohexyl-propionyl chloride |
| 16 | 2-(OCOCH₃)-phenyl | Cyclohexyl | (CH₂)₂ | 5,8 | 61 (Base) | 13,1 g N—(2-Acetoxy-phenyl)-piperazine and 10,5 g 3-Cyclohexyl-propionyl chloride |
| 17 | 2-(SCH₃)-phenyl | Cyclohexyl | (CH₂)₂ | 8,5 | 111–113 (HCl-Salt) | 10,5 g N—(2-Mercapto-phenyl)-piperazine and 12,5 g 3-Cyclohexyl-propionyl chloride |
| 18 | 2-(OH)-phenyl | Cyclohexyl | (CH₂)₂ | 6,1 | 128–130 (Base) | 10,7 g N—(2-Hydroxy-phenyl)-piperazine and 10,5 g 3-Cyclohexyl-propionyl chloride |
| 19 | 4-(CH₃O)-phenyl | Cyclohexyl | (CH₂)₂ | 15,0 | 173–175 (HCl-Salt) | 7,8 g 3-Cyclohexyl-propionyl and 9,6 g N—(4-Methoxy-phenyl)-piperazine |
| 20 | 2,6-(CH₃)₂-phenyl | Cyclohexyl | (CH₂)₂ | 6,9 | 73–74 (Base) | 11,4 g N—(2,6-Dimethyl-phenyl)-piperazine and 10,5 g 3-Cyclohexyl-propionyl chloride |
| 21 | 2-(CH₃)-phenyl | Cyclohexyl | (CH₂)₂ | 8,6 | 158 (HCl-Salt) | 10,5 g N—(2-Methyl-phenyl)-piperazine and 10,5 g 3-Cyclohexyl-propionyl chloride |
| 22 | 2-(Cl)-phenyl | Cyclohexyl | (CH₂)₂ | 6,5 | 114–117 (HCl-Salt) | 11,8 g N-(2-Chloro-phenyl)-piperazine and 10,5 g 3-Cyclohexyl-propionyl chloride |

-continued

| Example | R₁ | R₂ | alk | Yield in g | M.P. (0° C.) | Starting Materials |
|---|---|---|---|---|---|---|
| 23 | 2-F-phenyl | Cyclohexyl | (CH₂)₂ | 11,9 | 134–136 (HCl-Salt) | 10,8 g N—(2-Fluoro-phenyl)-piperazine and 10,5 g 3-Cyclohexyl-propionyl chloride |
| 24 | 2-Br-phenyl | Cyclohexyl | (CH₂)₂ | 7,0 | 52–54 (Base) | 14,5 g N—(2-Bromo-phenyl)-piperazine and 10,5 g 3-Cyclohexyl-propionyl chloride |
| 25 | 3-CF₃-phenyl | Cyclohexyl | (CH₂)₂ | 7,0 | 160–162 (HCl-Salt) | 13,8 g N—(3-Trifluoromethyl-phenyl)-piperazine and 10,5 g 3-Cyclohexyl-propionyl chloride |
| 26 | 2-NO₂-phenyl | Cyclohexyl | (CH₂)₂ | 15,3 | 61–62 (Base) | 12,4 g N—(2-Nitro-phenyl)-piperazine and 10,5 g 3-Cyclohexyl-propionyl chloride |
| 27 | 2-NH₂-phenyl | Cyclohexyl | (CH₂)₂ | 4,5 | 202–203 (HCl-Salt) | 8,8 g N—(2-Amino-phenyl)-piperazine and 7,8 g 3-Cyclohexyl-propionic acid |
| 28 | 2-NHCH₃-phenyl | Cyclohexyl | (CH₂)₂ | 6,5 | 89–91 (Base) | 11,5 g N—(2-Methylamino-phenyl)-piperazine and 10,5 g 3-Cyclohexyl-propionyl chloride |
| 29 | 2-N(CH₃)₂-phenyl | Cyclohexyl | (CH₂)₂ | 4,3 | Oil Rf-Value 0,72* | 12,2 g N—(2-Dimethylamino-phenyl)-piperazine and 10,5 g 3-Cyclohexyl-propionyl chloride |
| 30 | 2-N(C₂H₅)₂-phenyl | Cyclohexyl | (CH₂)₂ | 8,5 | 77 (Base) | 13,9 g N—(2-Diethylamino-phenyl)-piperazine and 10,5 g 3-Cyclohexyl-propionyl chloride |
| 31 | 2-NHCOCH₃-phenyl | Cyclohexyl | (CH₂)₂ | 6,2 | 107–108 (Base) | 13,1 g N—(2-Acetamino-phenyl)-piperazine and 10,5 g 3-Cyclohexyl-propionyl chloride |
| 32 | 2-NHCOC₂H₅-phenyl | Cyclohexyl | (CH₂)₂ | 6,0 | 93–94 (Base) | 13,1 g N—(2-Propionylamino-phenyl)-piperazine and 10,5 g 3-Cyclohexyl-propionyl chloride |
| 33 | phenyl | Cyclohexyl | (CH₂)₂ | 9,5 | 175–177 (HCl-Salt) | 9,7 g Phenylpiperazine and 10,5 g 3-Cyclohexyl-propionyl chloride |

-continued

| Example | R₁ | Product R₂ | alk | Yield in g | M.P. (0° C.) | Starting Materials |
|---|---|---|---|---|---|---|
| 34 | (pyridyl, N at bottom) | Cyclohexyl | (CH₂)₂ | 9,2 | 89–90 (Base) | 9,8 g N—Pyridyl-(2)-piperazine and 10,5 g 3-Cyclohexyl-propionyl chloride |
| 35 | (pyrimidyl) | Cyclohexyl | (CH₂)₂ | 7,1 | 104–105 (Base) | 9,8 g N—Pyrimidyl-(2)-piperazine and 10,5 g 3-Cyclohexyl-propionyl chloride |
| 36 | (chloropyrazinyl, Cl substituent) | Cyclohexyl | (CH₂)₂ | 10,7 | 95–96 (Base) | 19,8 g N—2-Chlor-pyrazinyl-(6)-piperazine and 10,5 g 3-Cyclohexyl-propionyl chloride |

*The RF-Value (from the English retention factor) was determined on a silica-gel-thin layer chromatography plate (Si60$_{F254}$Fa. Merck, Darmstadt), Running agent: Chloroform/Methanol/NH₃ at a ratio of 95:4:1.

Example 37

1-(2-Methylamino-phenyl)-4-(3-cyclohexylpropionyl)-piperazine (The same compound as obtained in Example 28)

There was dropped into a mixture of 0.03 mole (10.4 grams) of 1-(2-aminophenyl)-4-(3-cyclohexyl-propionyl)-piperazine and 0.12 mole (10.1 grams) of NaHCO₃ in 50 ml of water at 10° C. 0.11 mole (13.9 grams) of dimethyl sulfate. After the end of the dropping in, the mixture was allowed to slowly warm to room temperature. Then it was stirred for a further 24 hours at room temperature. Subsequently it was heated to 50° C. for 4 hours. After cooling to room temperature the mixture was treated with 10% NaOH until alkaline reaction. It was shaken three times, each time with 100 ml of diethyl ether, the organic phase separated off, the combined organic phases dried over Na₂SO₄ and concentrated in a vacuum. The concentrated residue was chromatographed over silica gel. As running agent there was employed CHCl₃/ethyl acetate in the ratio 95:5.

Yield: 2.1 grams.
M.P. 89°–91° C.

The alkylation can also be carried out with methyl iodide.

At room temperature with stirring there was dropped into a mixtured of 0.02 mole (2.8 grams) of K₂CO₃ and 0.018 mole (5.5 grams) of 1-(2-aminophenyl)-4-(3-cyclohexyl-propionyl)-piperazine dissolved in 75 ml of absolute tetrahydrofurane, 0.02 mole (2.84 grams) of methyl iodide dissolved in 20 ml of tetrahydrofurane. The mixture was heated at reflux for 7 days. The the solids formed were removed by suction filtering, the filtrate was washed with water, concentrated in a vacuum, and the concentrated residue chromatographed on silica gel. As running agent there was employed a mixture of diethyl ether/benzine in the ratio 1:1.

Yield: 1.6 grams.
M.P. 90°–91° C.

Example 38

1-(2-Propyloxy-phenyl)-4-(3-cyclohexylpropionyl)-piperazine (The same compound was obtained as in Example 11.)

0.03 mole (0.7 gram) of sodium was dissolved in 50 ml of absolute ethanol. There was added with stirring at room temperature 0.025 mole (7.9 grmas) of 1-(2-hydroxy-phenyl)-4-(3-cyclohexylpropionyl)-piperazine and the mixture heated at reflux for 1 hour with stirring. The solvent was then drawn off in a vacuum and the residue dissolved in 70 ml of absolute dimethyl formamide. There was dropped into this solution 0.025 mole (3.1 grams) of n-propyl bromide in 10 ml of dimethyl formamide at room temperature. Then the mixture was heated for 8 hours at 40°–50° C. The mixture was then concentrated in a vacuum, a residue treated with water, treated with ammonia until alkaline reaction, shaken 3 times, each time with 50 ml of CHCl₃, the organic phase dried over Na₂SO₄ and concentrated in a vacuum. The crude product was chromatographed on silica gel. As running agent there was used a mixture of ethyl acetate/CHCl₃ (5:95).

Yield: 2.6 grams.
M.P. of the hydrochloride: 146° C.

If there is used in place of n-propyl bromide 0.025 mole of another alkylated compound, there is obtained a different alkylated product.

Thus there are obtained according to the above-mentioned procedure using 0.025 mole (3.15 grams) of benzyl chloride 5.1 grams of the compound made in Example 15.

M.P. of the base: 86°–87° C.

Using 0.025 mole (3.02 grams) of allyl bromide there are obtained 5.0 grams of the compound made in Example 13.

M.P.: 37°–39° C.

Using 0.025 mole (4.07 grams) of cyclohexyl bromide there are obtained 1.8 grams of the compound made in Example 14.

M.P.: 70°–72° C.

Example 39

1-(3-Methoxy-phenyl)-4-(3-cyclo hexyl-propionyl)-piperazine

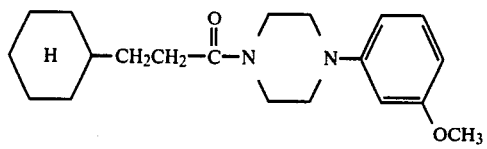

0.01 mole (2.8 grams) of N-(bis-(2-chloroethyl))-3-cyclohexyl-propionamide and 0.03 mole (1.2 grams) of 3-methoxy-aniline were heated in 50 ml of diethylene glycol dimethyl ether for 14 hours at 150° C. The mixture obtained was treated with water and subsequently extracted 3 times with dichloromethane. The combined methylene chloride extracts were dried over $Na_2SO_4$; after filtering off the solids, the filtrate was concentrated in a vacuum. The residue was taken up in 10 ml of acetone and treated dropwise with 3 ml of 6N isopropanolic hydrochloric acid. The hydrochloride precipitated and was recrystallized from methyl ethyl ketone.

Yield: 1.1 grams.

M.P. of the hydrochloride: 175°–176° C.

EXAMPLES OF PHARMACEUTICAL PREPARATIONS

Example, Capsules 10 kg of the compound made in Example 2 (hydrochloride) were granulated in known manner in a fluidized bed-spray granulation apparatus with a solution of 0.25 kg of gelatin in 2.25 kg of water. After mixing in 0.80 kg of cornstarch, 0.1 kg of magnesium stearate and 0.05 kg of highly dispersed silica, the mixture was filled into size 1 hard gelatin capsules in an amount in each sae of 224 mg.

Each capsule contains 200 mg of active material.

Example, Ampoule 100 grams of the compound made in Example 2 (hydrochloride) were dissolved in a mixture of 900 grams of propanediol-1,2 and 150 grams of ethanol. For injection purposes the solution was filled up to 2 liters with water, sterile filtered via a membrane filter of suitable pore size and filled into 2 ml sterilized ampoules under aseptic conditions.

One ampoule contains 100 mg of active material in 2 ml of solution.

What is claimed is:

1. A compound of the formula:

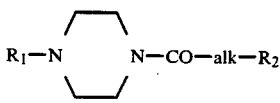

where $R_1$ is a phenyl group, pyridyl group, pyrimidyl group, or pyrazinyl group or a phenyl group, pyridyl group, pyrimidyl group, or pyrazinyl group having not more than one $R_3$ and not more than one $R_4$ group attached thereto where $R_3$ and $R_4$ are hydrogen, fluorine, chlorine, bromine, trifluoromethyl, hydroxyl, $C_1$–$C_6$-alkyl groups, $C_1$–$C_6$-alkoxy groups, $C_3$–$C_6$-alkenyloxy groups, $C_3$–$C_6$-cycloalkyloxy group, phenyl-$C_1$–$C_4$-alkoxy groups, $C_1$–$C_6$-alkylmercapto groups, the nitro group, the amino group, $C_1$–$C_6$-alkylamino groups, $C_1$–$C_6$-dialkylamino groups, $C_2$–$C_6$-alkanoyl groups, $C_2$–$C_6$-alkanoylamine groups or $C_2$–$C_6$-alkanoyloxy groups and $R_2$ is the adamentyl group, the 3,3-dimethylbicyclo[2.2.1]hept-2-yl group or, a saturated $C_3$–$C_7$-cycloalkyl group and alk is a $C_1$–$C_6$-alkylene chain and the pharmaceutically acceptable salts thereof.

2. A compound according to claim 1 where $R_1$ is a phenyl group or a phenyl group substituted in the 2-position by fluorine, a $C_1$–$C_6$-alkoxy group, a $C_2$–$C_6$-alkanoyloxy group or a $C_2$–$C_6$-alkanoylamino group, the group alk has 2-4 carbon atoms and $R_2$ is a $C_5$–$C_7$-cycloalkyl group and the pharmaceutically acceptable salts thereof.

3. A compound according to claim 2 where R is a phenyl group substituted in the 2 position by fluorine, a $C_1$–$C_6$-alkoxy group, a $C_2$–$C_6$-alkanoyloxy group, or a $C_2$–$C_6$-alkanoylamino group.

4. A medicinal composition comprising a compound of claim 1 together with a carrier, diluent, or adjuvant.

5. A process of treating a mammal in need of an analgestic, an ulcer preventive agent, an antiphlogestic agent, or an agent which arrest the secretion of gastric juice comprising administering to the mammal a compound according to claim 1 in an amount effective for such purpose.

6. A process of treating a mammal in need of an analgetic comprising administering to the mammal an analgesically effective amount of a compound of claim 1.

7. A process of treating a mammal in need of an analgestic, an ulcer preventive agent, an antiphlogestic agent, or an agent which arrest the secretion of gastric juice comprising administering to the mammal a compound according to claim 2 in an amount effective for such purpose.

8. A process of treating a mammal in need of an analgestic, an ulcer preventive agent, an antiphlogestic agent, or an agent which arrest the secretion of gastric juice comprising administering to the mammal a compound according to claim 3 in an amount effective for such purpose.

9. A process of treating a mammal in need of an analgestic comprising administering to the mammal an analgesically effective amount of a compound of claim 2.

10. A process of treating a mammal in need of an analgestic comprising administering to the mammal an analgesically effective amount of a compound of claim 3.

* * * * *